United States Patent [19]

Monroy

[11] Patent Number: 4,681,543
[45] Date of Patent: Jul. 21, 1987

[54] RAPID DENTURE TECHNIQUE

[75] Inventor: Enrique A. Monroy, Hialeah, Fla.

[73] Assignee: Dentsply Research & Development Corp., Milford, Del.

[21] Appl. No.: 829,746

[22] Filed: Feb. 14, 1986

[51] Int. Cl.[4] ............................................. A61C 13/10
[52] U.S. Cl. .................................. 433/196; 433/167; 433/214; 264/18
[58] Field of Search .............. 433/167, 171, 191, 196, 433/197, 199, 202, 212, 213, 214; 264/16, 17, 18

[56] References Cited

U.S. PATENT DOCUMENTS

| | | | |
|---|---|---|---|
| 1,518,075 | 12/1924 | Kesling | 433/196 |
| 2,059,262 | 11/1935 | Meyer | 433/213 |
| 2,229,780 | 1/1941 | Vaillancourt | 433/196 |
| 3,413,724 | 12/1968 | Segal | 433/214 |
| 3,644,996 | 2/1972 | Weinkle | 433/171 |
| 3,971,133 | 7/1976 | Mushabac | 433/213 |
| 4,161,065 | 7/1979 | Gigante | 433/214 |
| 4,247,287 | 1/1981 | Gigante | 433/199.1 |
| 4,370,135 | 1/1983 | Powell | 433/213 |
| 4,457,713 | 7/1984 | Schneider | 433/171 |
| 4,470,815 | 9/1984 | Hazar | 433/171 |
| 4,533,325 | 8/1985 | Blair et al. | 433/171 |
| 4,551,098 | 11/1985 | Blair | 433/171 |

Primary Examiner—John J. Wilson
Attorney, Agent, or Firm—Edward J. Hanson, Jr.; C. Hercus Just

[57] ABSTRACT

A technique by which a denture formed from light-curable plastic material, and including individually positioned artificial teeth, is produced by the use of a custom, substantially U-shaped, matrix formed from an elongated shape of light-curable plastic material which is impressed into and is releasably affixed to the incisal and occlusal surfaces of the teeth when mounted in set-up wax on a model of a patient's gum. The matrix, while so affixed to the teeth, is light-cured to permit the connected matrix and teeth to be separated from the wax while the teeth are maintained by the matrix in accurate desired interrelation while the teeth are being formed into a final denture by sculpturing light-curable denture material between the denture base and teeth to interconnect the exposed ridge-lap ends of the teeth upon the matrix to the denture material while the matrix maintains the teeth in desired adjacent relationship for engagement by and affixation to the denture material as sculptured into the final denture shape, which is then light-cured and the matrix is separated from the incisal and occlusal surfaces of the teeth on the completed denture.

17 Claims, 22 Drawing Figures

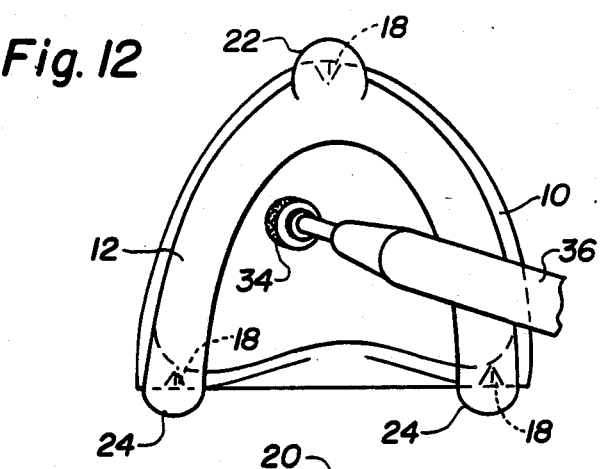
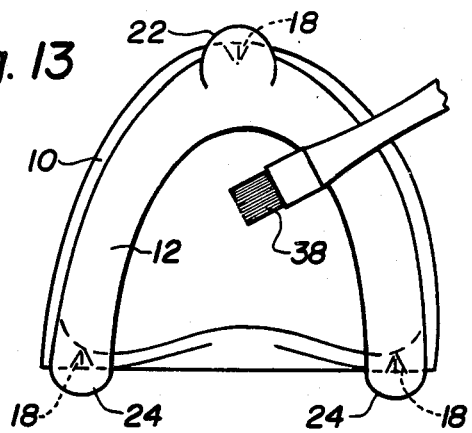
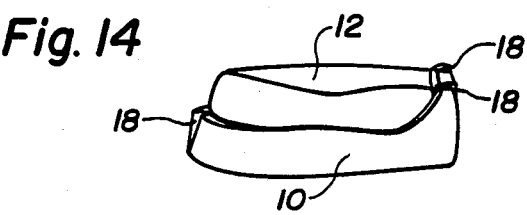
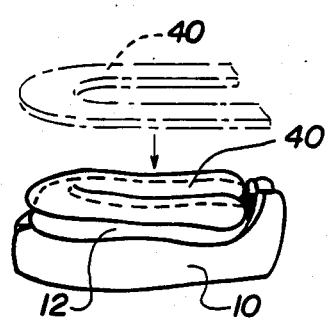
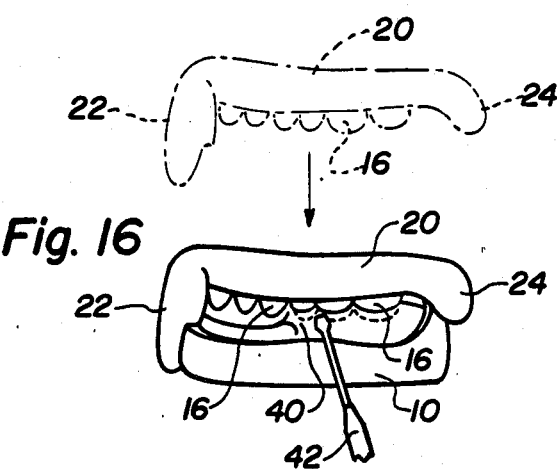
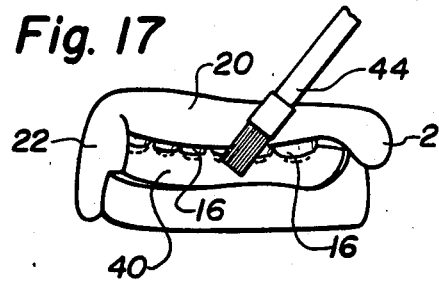
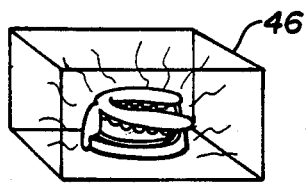
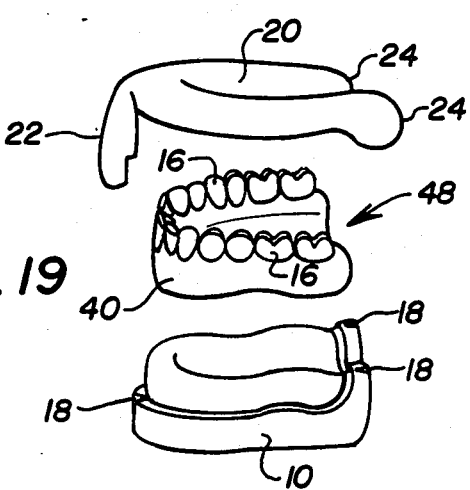

RAPID DENTURE TECHNIQUE

BACKGROUND OF THE INVENTION

This invention pertains to a technique and certain elements which have been developed to effect a technique of producing a denture rapidly in final form from start to completion. Many attempts have been made to do this previously, certain of which comprise the subject matter of prior U.S. Pat. Nos.:
3,644,996—Weinkle; Feb. 29, 1972
4,161,065—Gigante (1); July 17, 1979
4,247,287—Gigante (2); Jan. 27, 1981
4,457,713—Schneider; July 3, 1984
4,470,815—Hazar; Sep. 11, 1984

Nothing is known at present about the success or failure of the subject matters of the foregoing patents relative to the Dental Profession but, as far it is known, none of them have met with any extensive success as far as being widely adapted by the dental profession as concerned.

More recently and especially since the development of, suitable light-curable dental material for the dental profession, has become quite widely used, Dentsply International of York, Pennsylvania has developed procedure and apparatus to completely produce dentures which employ such light-curable materials. These developments comprise the subject matter of U.S. Pat. No. 4,533,325 by Blair, et al entitled Method and Apparatus to Produce Artificial Dentures, issued Aug. 6, 1985. A second invention of said company comprises a companion of the invention forming the subject matter of the above-cited patent and is the subject matter of U.S. Pat. No. 4,551,098 in the name of Blair, issued Nov. 5, 1985, and during the pendency thereof, divisional application Ser. No. 735,597 was filed May 20, 1985, now U.S. Pat. No. 4,609,351, issued 09/02/86 and a combination divisional and CIP application of said U.S. Pat. No. 4,551,098 bearing Ser. No. 702,816 was filed Feb. 19, 1985.

The subject matter of said aforementioned inventions developed by Dentsply International Inc., primarily is based upon the use of a full arch form of artificial teeth which preferably are manufactured in a two-part mold as distinguished from a three-part or other form of mold. To accomplish this, compromises in the shapes of the teeth had to be made to render them adaptable for formation by two-part molds. It has been found that when this development was introduced to the dental profession recently, it did not meet with the success that had been hoped for, due particularly to the desire of at least certain members in the dental profession to include more life-like tooth shapes and arrangements in the completed dentures. This situation, coupled with the present availability of certain well-accepted dental materials capable of being matured by visible light, has resulted in the present invention being developed, details of which are set forth below.

SUMMARY OF THE INVENTION

It is among the primary objectives of the present invention to provide a technique and certain apparatus by which artificial dentures can be fabricated rapidly by the use of light-curable dental materials. By an aspect of the invention, steps are provided in a technique by which sets of separate, individual teeth, preferably of desired life-like configuration, may be mounted on models to reproduce a natural arrangement of artificial teeth in a denture for any individual patient, similar to arrangements employed at present in wax set-ups on denture models which have been utilized by dentists and laboratories for many years.

Another object of the invention is to employ, basically, the rudiments of denture components and ancillary items which have long been used in dentistry but in regard to which certain novel digressions are employed in the instant technique such as the use of light-curing dental materials which permit the formation of highly desirable life-like dentures in as short a time as two and one half hours or less, from start to completion after the plaster model has been provided.

A further object of the invention is to provide a technique including relatively simple and limited steps which result in the formation of highly desirable dentures; said technique essentially to include the steps of: (a) accurately conforming a piece of pliable denture base sheet material of light-curable nature to a plaster cast or model of a patient's gum, and then trimming and light-curing the same; (b) applying set-up wax to said cured denture base; (c) mounting a set or partial set of individual, preferably life-like artificial teeth upon the set-up wax; (d) forming a matrix of somewhat rope-like, light-curable, pliable, denture material into a configuration complimentary to that of the teeth mounted in the wax set-up; (e) providing a leg of the same material as the matrix and connecting one end of the same to the matrix mid-way of the ends thereof and extending perpendicularly therefrom; (f) impressing said pliable light-curable matrix against the exposed incisal and occulsal surfaces of the teeth in the wax to detachably secure the teeth to the matrix; (g) impressing the free ends of the matrix against the opposite sides of the rear end of the model and also impressing the free end of the leg on the mid-portion of the matrix against the model incident to forming inter-engagable positioning means between the matrix and model; (h) light-curing the matrix while impressed against the aforementioned teeth; (i) removing the wax by customary or other means from the denture baseplate and teeth which are connected to the matrix, and of which the ridge-lap ends of the teeth are exposed after removal of the wax; (j) separating the matrix and teeth therein from the cured denture base and applying pliable light-curable denture base material to the crest of the cured denture base and preferably, somewhat at least, roughly contour the same to resemble a denture prior to (k), repositioning the matrix with the teeth thereon, relative to the model thereby disposing the ridge-lap ends of the teeth firmly into the added denture base material, followed by (1) completing the sculpturing of the denture into final form especially in regard to the ridge-lap ends of the teeth which now firmly engage the final denture base material; (m) light-curing the resulting denture upon the model while the matrix is attached thereto; and (n) removing the matrix from the teeth which now are firmly anchored to the completed denture and then otherwise polishing and finalizing the denture which is ready for insertion.

Details of the foregoing technique and especially of the matrix which comprises the mechanism employed with the technique are set forth in the following specification and illustrated in the accompanying drawings comprising a part thereof.

BRIEF DESCRIPTION OF THE DRAWINGS

FIG. 1b is a top plain view of the model shown in FIG. 1a.

FIG. 6b shows the matrix componets assembled and impressed against the teeth of the model shown in FIG. 6a.

FIG. 9a is an exemplary illustration of one means by which wax is removed from the combination shown in FIG. 6a.

FIG. 12 is a perspective view illustrating the step of roughening the denture base with a carbide cutter or otherwise to assure complete removal of the wax therefrom.

FIG. 13 is a perspective view illustrating the application of heat-curable monomer to the denture base by brushing or the like.

FIG. 14 is an exploded view illustrating the removal of the matrix from the pattern and the cured denture base member thereon.

FIG. 15 is an exploded diagramatic illustration showing the application of additional, pliable, light-curable dental plastic material from which the finished portion of the denture is formed which engages the ridge-lap surfaces and adjacent areas of the teeth in the final denture.

FIG. 16 is an exploded view showing the pressing of the teeth on the matrix into the ridge of light-curable denture material which has been applied to the cured denture base member and then is in process of the denture material being sculptured into the final shape of the denture.

FIG. 17 is a diagramatic illustration showing the application by brush, of an air barrier coating applied to the attached teeth and light-curable plastic denture material which has been sculptured into final form.

FIG. 18 diagramatically illustrates the subjection of the combined structure of FIG. 17 being subjected to visible light to cure and bond the denture material to the teeth and the denture base member incident to forming the completed denture.

FIG. 19 is an exploded view illustrating the final step of separating the matrix from the teeth which are bonded to the denture material and denture base. The completed denture has been removed from the plaster model.

DETAILED DESCRIPTION OF THE PREFERRED EMBODIMENTS OF THE INVENTION

Figure 1A:
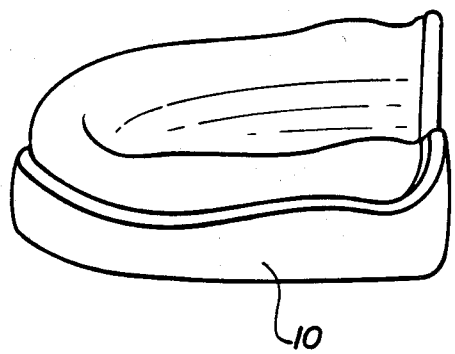
FIG. 1a is a perspective side view of a conventional dental model of a patients gum usually formed from gypsum material.
Figure 1B:
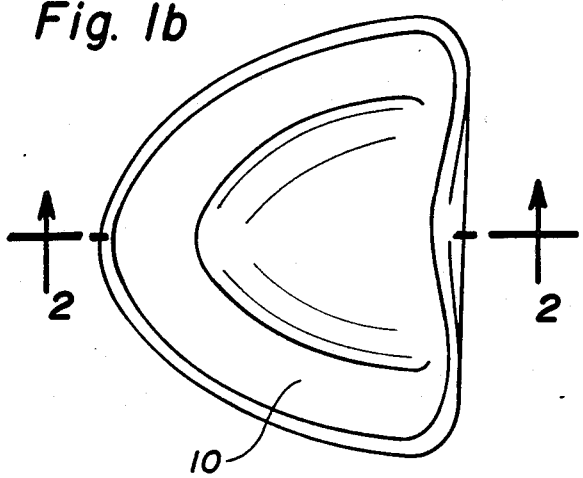
Figure 2:
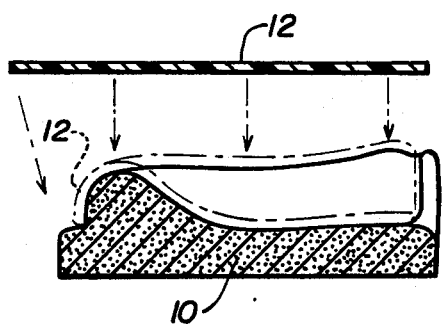
FIG. 2 is an expanded vertical sectional view seen on line 2—2 of FIG. 1b that illustrates a sheet of denture base material being adapted to the model.

Referring to FIGS. 1a–1b, there is illustrated therein a custom model of an individual patient's gum; the same usually being formed from hard gypsum material or the like. Referring to FIG. 2, there is applied to the contoured surface of the model 10, a sheet of light-curable denture base material 12 which is faithfully contoured to the custom surface of the model and at this stage is suitably trimmed at the edges to correspond to the model 10 and then is light-cured by visible light of suitable intensity. This renders the baseplate member 12 rigid and the surface thereof, which is next to the model, becomes the acutual surface which engages the patient's gum.

Figure 3:
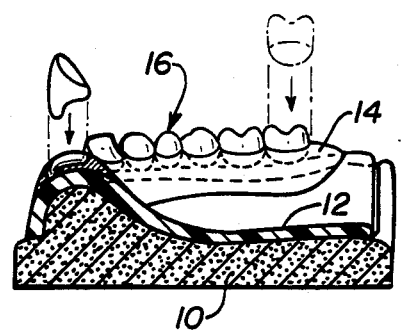
FIG. 3 is a vertical sectional view partially similar to that of FIG. 2 and illustrating wax applied to the denture base and a set of separate, individual artificial teeth being applied to the wax.

Referring to FIG. 3, the next step is illustrated in which a suitable amount of dental set-up wax is applied as a temporary set-up material to the tooth receiving area or ridge area of the denture base member shown in phantom in FIG. 2 and also in FIG. 3; said view also illustrates the additional step of positioning a standard set of separate anterior and posterior artificial teeth 16 into the wax 14 in any desired, life-like arrangement which may be achieved by the dentist or dental technician. There is some tendency at present, where practical, to arrange a set of artificial teeth in similar configuration to the appearance of the former natural teeth of a patient which the artificial teeth are replacing.

Figure 4:
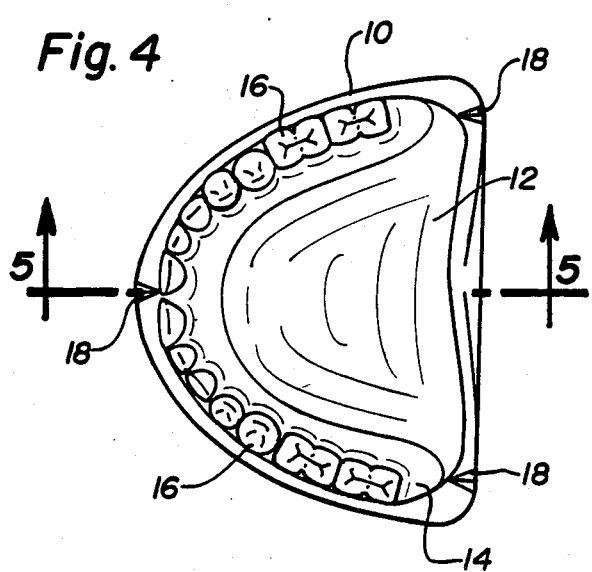
FIG. 4 is a top plan view of the composite arrangement shown in FIG. 3 and further illustrating parts of sets of positioning means formed on the model.
Figure 5:
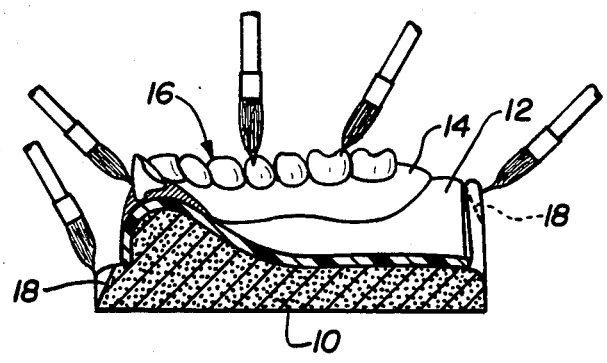
FIG. 5 is a view similar to FIG. 3 but illustrating diagramatically the application of parting material being brushed onto the teeth on the model.

At this stage of the technique, it is preferred that certain positioning elements be formed in model 10, as shown in FIG. 4, which conveniently may comprise notches 18 which are scratched, or otherwise formed in the plaster comprising the model for purposes to be described. Following the formation of the notches, the assembly thus far achieved is subjected to the application of a liquid dental separator material of a conventional type which may be applied by brushes, or otherwise, as indicated in exemplary manner in FIG. 5.

Figure 6A:
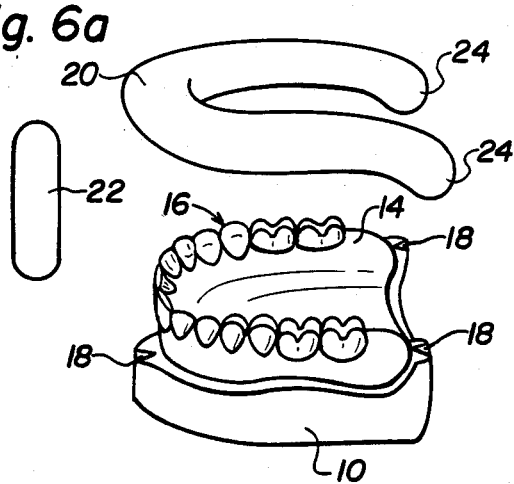
FIG. 6a is an exploded view showing the model illustrated in FIGS. 3–6 in the process of having matrix components shaped thereto.
Figure 6B:
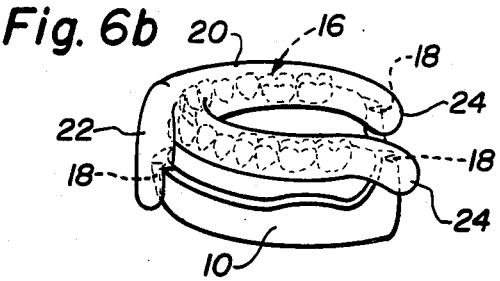

Except for the formation of the light-cured denture base member 12 and the forming of the positioning notches 18, the steps otherwise performed, as described above, are substantially of conventional nature. Departure from conventional means and method is undertaken at this stage by forming a matrix 20 which initially may be in the elongated form of suitable length so that it may be configured to be complementary to the arrangement of teeth 16 supported by the wax 14 on model 10. There is also fixed to the matrix form 20, mid-way of the front portion thereof, a support member or leg 22 which preferably is formed from the same material as the matrix 20; said material being a light-curable plastic material in pliable form. After the leg 22 has been attached to the matrix 20, as shown in FIG. 6b, the soft matrix material is impressed downwardly upon the full complement of teeth 16 in the model 10 so as to be attached to and somewhat encapsulate the exposed incisal and occlusal surfaces, collectively, the biting ends of the teeth 16. Before the matrix is light-cured, the free ends of the shaped matrix are extended downward into firm abutting relationship with the opposite side portions of the rear end of the model 10 so that portions of the material are impressed into the notches 18 and thereby form cooperating, complementary positioning members or means in association with the notches 18. Further, the lower portion of the leg 20, likewise, is impressed against the mid-portion of the front end of the model 10 so as to impress part of the material into the front notch 18 on the model and thus form a cooperating detent which serves as additional positioning means. The portions of the matrix 20 engaged with the model 10 which in turn engage with the denture base member 12, provide positioning means between the matrix and the denture base member. From this, it will be seen that the matrix 20 is provided with a triangular or three-point arrangement of support and positioning means; the usefulness of which is described hereinafter.

Figure 7:
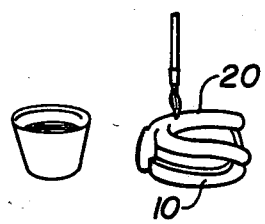
FIG. 7 is a diagramatic illustration of the combined arrangement of FIG. 6b being coated with liquid air barrier material.
Figure 8:
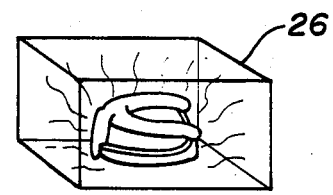
FIG. 8 is diagramatic illustration of the combination shown in FIG. 6b being subjected to intense visible light to cure the light-curable matrix, thereby rigidifying the same.

As diagramatically illustrated in FIG. 7, the matrix 20 which is in place upon the model 10 and the teeth thereon, preferably is coated exteriorly with a liquid air barrier material which can be applied by a brush as shown in said figure. After such coating, the assembly shown in FIG. 6b is placed in a suitable source of preferably intense visible light, represented by the enclosure 26 in FIG. 8. In the preferred technique, the light is supplied by one or more lamps capable of producing intense visible light (such lamps not being shown) and such light need only be used for a very brief period of only a few minutes for purposes of curing the light-curable material from which the matrix 20 is formed. This renders the matrix rigid for manual handling.

Figure 9A:
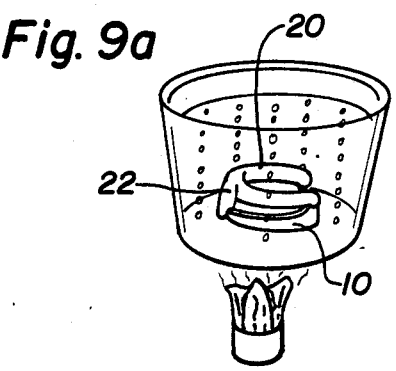
Figure 9B:
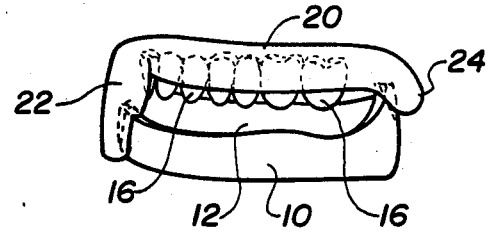
FIG. 9b illustrates a side elevation of the matrix supporting the artifical teeth in spaced relationship to the conformed denture base from which wax has been removed.

At this stage, the assembly shown in FIG. 6b, for example, still contains the set-up wax 14 and it is now desirable to remove the same, which may be done in any conventional manner such as illustrated in FIG. 9a in the exemplary form of a hot water bath, during which time the matrix 20, the teeth 16 connected thereto, and the cured denture base member 12 remains attached to the model 10. Following such removal of the wax, an assembled arrangement is produced, as illustrated in FIG. 9b, comprising matrix 20, model 10, denture base member 12, which previously has been light cured, and the artificial teeth 16 which are firmly but detachably supported by the matrix 20 and now the exposed ridge-lap surfaces of the teeth are connected to the denture base member 12 by the use of suitable light-curable, denture-forming plastic material as described in detailed hereinafter.

Figure 10:
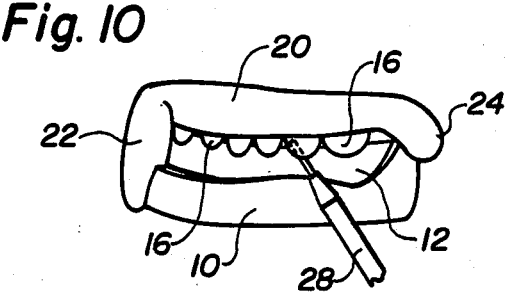
FIG. 10 is a diagramatic illustration of roughing the ridge-lap surfaces of the teeth supported by the matrix in spaced relationship to the ridge-lap on the model.
Figure 11:
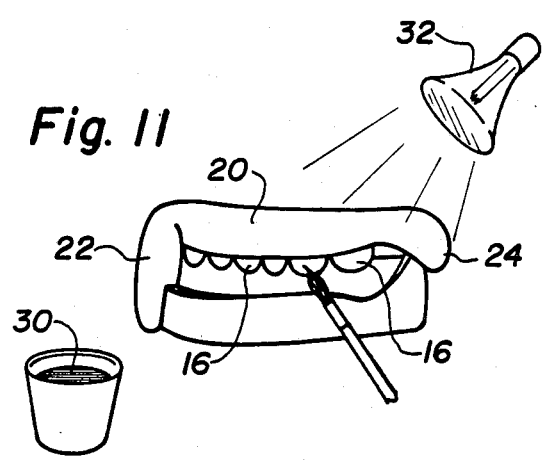
FIG. 11 is an exploded perspective view illustrating the step of applying a liquid, light-sensitive, bonding agent to the teeth supported by the matrix and curing the same by visible light.

Referring to FIG. 10, it is preferred in accordance with the present invention, to roughen the exposed ridge-lap surfaces of the teeth 16 which may be done by an appropriate, suitable dental bur, operated by handpiece 28. Following such roughening, referring to FIG. 11, it will be seen that the roughened ridge-lap surfaces of the teeth have light-sensitive, liquid bonding agent 30 applied to the teeth 16 and the same is cured by an appropriate source of visible light 32. The depiction in FIG. 11, as with the other illustrative depictions, is illustrative only, it being understood that after the ridge-lap surfaces of the teeth have been thoroughly covered with the light-sensitive liquid bonding agent the light rays must be brought into engagement with all of the bonding agent covered surfaces to effect curing of the bonding agent. Appropriately the matrix 20 with the teeth 16 connected to it may be lifted off of the model 10 and turned up toward the light or the light will otherwise be positioned relative to the ridge-lap surface to obtain the desired curing of the light sensitive liquid bonding agent.

The next preferred step in the technique is to roughen the upper, exposed surface of the denture base member 12 by an appropriate dental bur 34 carried by handpiece 36, as shown in FIG. 12, primarly for purposes of insuring complete removal of all wax therefrom. Following this, the roughened surface of the denture base member 12 has a suitable heat-curable monomer applied liberally thereto by a brush 38, such as shown in FIG. 13.

At this stage of the technique, as shown in FIG. 14, the matrix 20 with the teeth 16, firmly but separably supported thereon, is removed from the model 10 and the cured denture base member 12 is positioned thereon in operative manner. As shown in FIG. 15 in phantom, a desired amount of soft, light-curable plastic denture material 40 is applied to the ridge of the cured denture base member 12 and contoured somewhat into a ridge configuration preferably, at least partially, resembling the final anatomy or shape of the finished denture. Then, referring to FIG. 16, the matrix 20 with the teeth 16 supported thereby, is repositioned upon the model 10 accurately, as controlled by the positioning means comprising notches 18 in the model 10 and the complementary detents which have been formed in support member 22 and the free ends 24 of matrix 20. By this means, very accurate positioning of the teeth upon the denture material 40 is achieved while the set of teeth are held in accurate position with respect to the denture base member 12 on model 10 and the denture material 40 which has been applied to the baseplate member 12. The denture material 40 is contoured to final stage by suitable dental tools of conventional nature, one of which is shown at 42.

As shown in FIG. 17, after the completion of the contouring of the light-curable denture material 40, the technique of the present invention preferably includes the application by means of a brush 44 of a liquid air barrier coating material to the teeth 16 on matrix 20 and the contoured denture material 40 into which the ridge-lap ends of the teeth 16 have been positioned and anchored firmly for bonding of the material 40 thereto. Care is taken to contour material 40 around the gingival edges of the teeth to form a natural appearance. Following this, the entire assembly shown in FIG. 17 is introduced to an enclosure 46 in which preferably high intensity visible light is discharged. This enclosure or compartment may be similar to that shown in FIG. 8 but is illustrated in FIG. 18 as an enclosure 46. The preferred source of the light is produced by appropriate lamps, not shown, of required capacity and intensity of visible light. The light-curing of the denture material 40 bonds the same to the teeth 16 as well as to the denture base member 12, comprising the innermost surface of the denture thus formed, whereby such bonding actually completes the physical formation of a unitary denture in final configuration.

Referring to FIG. 19, the final step of the technique comprises the removal of the matrix 20 from the completed and fully bonded denture 48; the latter readily being removeable from the gypsum model 10, and after usual polishing of the completed denture 48 it is ready for try-in and, if satisfactory, for actual delivery to the patient.

In one alternate variant technique, starting at the stage of the procedure shown in FIG. 15, a lesser amount of the pliable light-curable denture material 40 is applied to the ridge of the cured denture member 12 and shaped to the ridge in a configuration to receive the lap ends of the teeth held by the matrix 20. The matrix is then repositioned upon the model 10 accurately and the teeth are tacked or secured to the denture base member 12 by light-curing the denture material 40 in the manner shown in FIG. 18 or with other appropriate light-emiting means. The matrix 20 is then removed from the bite ends of the teeth. Then the final gingiva-forming procedure is undertaken by the addition of additional light-curable denture material about the buccal/labial portion of the denture. This additional denture material is shaped to the appearance of gingiva and then cured.

The technique of the present invention is illustrated in the drawings and detailed description, producing an upper denture, but lends itself equally to the production of lower dentures. The technique has been described with the use of a full set of individual teeth, which is where the greatest value is foreseen, but also has obvious advantageous uses with sets of preassembled teeth, a single tooth denture or prosthesis and with partial dentures. The preferred light-cured plastic materials are preferred; however, other materials are usable in proper circumstances. The matrix is described as encapsulating the bite ends of the teeth, but so long as the removeable connection is secure, encapsulation is not required. Encapsulation of the bite ends of the teeth is preferred because it provides a very stable, yet readily separable connection of the teeth with the matrix.

The materials and equipment used in practicing the present invention in the Detailed Description of the Preferred Embodiment of the Invention are commercially available from Dentsply International Inc.; the related Dentsply Research and Development Corporation being the assignee of this patent application. The materials are sold under the trademark TRIAD ®, with the exception of the heat-curable monomer applied in FIG. 13 which is sold under the trademark LUCITONE ®.

Experimental practice of the present invention has readily demonstrated that upon furnishing a model 10 of a patient's gum to a dentist or laboratory, a desirable light-cured denture may be fabricated and completed within a period of approximately two and one-half hours or less. It will be understood that the equipment required is not expensive and the technique primarily comprises procedural steps that also employ, what is believed to be, a novel custom matrix which faithfully preserves the pattern or positioning of individual teeth as positioned on the wax set-up. The pattern of teeth may be supported by the matrix for accurate removal from and repositioning upon the model. This is made possible by the separable connection of the incisal and occlusial portions of the teeth in the soft, conformable light-curable material 20 which, when light-cured, becomes fully rigid yet permits the separation of said encapsulated portions of the teeth when desired and especially when the ridge-lap surfaces on the teeth have been bonded firmly, cured to the denture base and the light-cured denture material bonded thereto.

The technique of forming the denture by providing the positive positioning of the matrix 20 in relation to the denture base member 12, by the model 10, and the three connecting members 24, 24 and 22, are related to one another in a generally triangular array for lateral and vertical accuracy of alignment, as shown in FIG. 19. The accurate repositioning of the matrix on the model is thereby provided. After the repositioning, which impresses the ridge-lap ends of the teeth in the light-curable material on the denture base ridge, the light-curable material can be shaped into natural-looking artificial gingiva before curing with actinic light, preferably in the visible spectrum.

By using individual, separate teeth, selected types, kinds and shapes of teeth may be employed and mounted in the denture base in a highly desirable life-like configuration as distinguished from other teeth having less life-like characteristics. Further, the only actual current, unorthodox equipment which is involved in the technique is the novel, very simple, inexpensive matrix which is made in custom manner for each individual denture.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms as shown herein.

I claim:

1. A technique for rapidly producing finished dentures upon which individual artificial teeth are mounted in life-like configuration; said technique comprising the steps of:
    a. forming a denture base of light-curable material on a model of a patient's gum having front and rear ends and light-curing said base thereon;
    b. applying set-up wax to the denture base;
    c. setting up separate artificial teeth of a set upon said wax in life-like configuration with the incisal and occlusal ends of the teeth exposed;
    d. forming a matrix of pliable light-curable material of elongated shape into complementary shape to said set of teeth;
    e. forming a short leg of said elongated material and affixing one end of it to the mid-point of the front end of said matrix and depending it therefrom for engagement with said model;
    f. impressing said pliable matrix against the exposed incisal and occlusal ends of said teeth to effect a releasable encapsulating connection of said teeth to said matrix and extending the free ends of the matrix against the rear end of the model and the free end of said leg against the front end of the model;
    g. light-curing said matrix to render the same rigid and manually manueverable;
    h. removing the wax from the denture base and teeth on the matrix;
    i. applying pliable light-curable denture material to the ridge of the denture base;
    j. impressing the exposed ridge-lap ends of said teeth on the matrix into said applied denture material and completely contouring the assembled teeth and material into final shape;
    k. light-curing the assembled teeth and material; and
    l. separating the matrix from a thus completed denture.

2. The technique according to claim 1 further including the step of forming interengageable positioning means respectively on the portions of said matrix which engage said model to permit removal of the matrix from the model and reconnection of the matrix to said model exactly in the original position of the matrix thereon.

3. The technique according to claim 1 including the additional step of initially forming notches in the rear end of said model respectively adjacent opposite sides thereof and forming another notch in the front end of the model mid-way thereof and including the still further step, while still uncured, of impressing against said notches, the portions of said matrix which engage the rear and front ends of said model for purposes of forming complementary detents in said impressed portions of the matrix and thus form interengageable positioning means which become rigid when the matrix is light-cured and thereby permit separation of the matrix from the model and reconnection thereof to the model exactly in the original position of the matrix thereon by engaging said detents in said notches.

4. The technique according to claim 1 including the further step of applying dental separator material to the exposed incisal and occlusal ends of the teeth on the model prior to impressing the pliable uncured light-curable material of the matrix against said teeth to insure separation of the matrix from the teeth when the denture has been completed.

5. For use in the fabrication of artificial dentures, a custom-formed matrix adapted to be shaped from an elongated form of pliable light-curable plastic dental material shaped complementarily to the disposition of a set of artificial teeth set in wax on a dental model, the outer ends of said form being shaped for engagement with said model at the rear end thereof, and a support member of the same material as said elongated form affixed to said form mid-way of the ends thereof and extending transversely thereto, the free end of said support member being adapted to engage the front end of said model whereby in cooperation with said outer ends of said form a minimum of a three point support of said matrix upon a dental model is provided, said matrix being adapted to be impressed upon exposed incisal and occlusal surfaces of a set of artificial teeth mounted upon a model for releaseable connection of said teeth to said matrix for support of said teeth independently of said model when desired and said formed matrix being rendered rigid when light-cured with said teeth releaseably connected thereto.

6. The custom-formed matrix according to claim 5 further characterized by said support member comprising a leg and said form of light-curable plastic material being generally U-shaped.

7. The custom-formed matrix according to claim 5 wherein the outer ends of said form and free end of said support member affixed to said form additionally have positioning means thereon adapted to releaseably engage and disengage complementary positioning means on said model to insure precise positioning of the matrix and teeth thereon when releaseably carried thereby relative to the model and portions of a denture positioned upon the model.

8. The custom-formed matrix according to claim 7 further characterized by the positioning means on said matrix comprising fixed dentents complementary to corresponding mating positioning means on said model comprising notches formed in said model.

9. A technique for rapidly producing a finished dental prosthesis upon which at least one artificial tooth is mounted in life-like position; said technique comprising the steps of:
a. forming a denture base member in a configuration having a tooth receiving area;
b. applying a temporary set-up material to the denture base member tooth receiving area;
c. setting up at least one artificial tooth having a biting end and receiving area end upon said temporary set-up material in life-like position with the biting end of the tooth exposed and the receiving area end of said tooth engaged toward said tooth receiving area;
d. forming a matrix of pliable material into complementary shape of said life-like position;
e. impressing said matrix against the exposed biting end of said tooth to effect a releaseable connection of said tooth to said matrix;
f. providing positioning means for positioning the matrix relative to the denture base member;
g. curing said matrix to render the same rigid and manually maneuverable;
h. removing said tooth releaseably connected with the matrix and exposing the receiving area end of said tooth;
i. shaping pliable denture material to the tooth receiving area of the denture base;
j. impressing the exposed receiving area end of said tooth while it is connected releaseably with the matrix on said shaped denture material;
k. curing said shaped denture material with said tooth impressed thereon; and
l. separating the matrix from said tooth.

10. The technique of claim 9 wherein said pliable material is light-curable and said curing of said matrix is by light.

11. The technique of claim 9 wherein said releaseable connection of said tooth to said matrix comprising a liquid dental separator material.

12. The technique of claim 9 wherein said positioning means comprising at least three connecting members, which are related to one another in a generally triangular array for lateral and vertical accuracy of alignment of the matrix and the denture base member upon repositioning and said impressing the exposed receiving area end of said tooth while it is releaseably encapsulated with the matrix into said shaped denture material comprising said repositioning.

13. The technique of claim 9 wherein said artificial tooth is included in a set of individual teeth including anterior and posterior teeth.

14. The technique of claim 9 wherein said shaping of pliable denture material to the tooth receiving area comprising placing light-curable material on said tooth receiving area.

15. The technique of claim 14 wherein after impressing the exposed receiving area end of said tooth while it is releaseably connected with the matrix into said shaped denture material, the shaped denture material is shaped into the appearance of gingiva and light-cured and thereafter the procedure of separating the matrix from said tooth is carried out.

16. The technique of claim 15 wherein said tooth receiving area is the ridge of said denture base member and the receiving area end of said artificial tooth is the ridge-lap end of said tooth and said pliable material forming a matrix is a light-curable material.

17. The technique of claim 14 wherein after impressing the exposed receiving area ends of said tooth while it is releaseably connected with the matrix into the denture material, the denture material is cured and thereafter additional denture material is added about the buccal/labial portion of the denture and said additional denture material is shaped to the appearance of gingiva and thereafter said additional denture material is cured.

* * * * *